US005693833A

United States Patent [19]
Falling et al.

[11] Patent Number: 5,693,833
[45] Date of Patent: Dec. 2, 1997

[54] PROCESS FOR THE REACTIVATION OF IODINE-CONTAINING CATALYSTS

[75] Inventors: Stephen Neal Falling; Patricia Lopez, both of Kingsport, Tenn.

[73] Assignee: Eastman Chemical Company, Kingsport, Tenn.

[21] Appl. No.: 701,932

[22] Filed: Aug. 26, 1996

[51] Int. Cl.[6] .................. B01J 20/34; C07D 307/28
[52] U.S. Cl. .................. 549/507; 502/24; 502/27; 556/104
[58] Field of Search .................. 549/507; 502/24, 502/27; 556/104

[56] References Cited

U.S. PATENT DOCUMENTS

| | | | |
|---|---|---|---|
| 3,544,608 | 12/1970 | Pande | 556/104 |
| 5,238,889 | 8/1993 | Falling et al. | 502/24 |
| 5,315,019 | 5/1994 | Phillips et al. | 549/507 |

*Primary Examiner*—Bernard Dentz
*Attorney, Agent, or Firm*—J. Frederick Thomsen; Harry J. Gwinnell

[57] ABSTRACT

Disclosed is a process for converting an iodine-free organotin (IV) compound resulting from the decomposition of an organotin (IV) iodide during the catalytic isomerization of $\gamma,\delta$-epoxyalkenes to 2,5-dihydrofurans to the corresponding, catalytically active organotin (IV) iodide by intimately contacting a catalyst mixture comprising (i) an organotin (IV) iodide, (ii) an iodine-free organotin (IV) compound resulting from the decomposition of the organotin (IV) iodide of component (i), and (iii) a solvent selected from hydrocarbons and chlorocarbons with aqueous hydrogen iodide.

10 Claims, No Drawings

PROCESS FOR THE REACTIVATION OF IODINE-CONTAINING CATALYSTS

This invention pertains to a process for the reactivation of catalysts which have lost a portion of their activity due to the loss of iodine. More specifically, this invention pertains to a process for restoring the activity of a catalyst composition comprising a mixture of one or more organotin (IV) iodide compounds and one or more iodine-free organotin (IV) compounds.

The preparation of γ,δ-epoxyalkenes by the selective monoepoxidation of butadiene and analogous dienes is described in U.S. Pat. Nos. 4,897,498 and 4,950,773. U.S. Pat. No. 5,082,956 discloses processes for the preparation of 2,5-dihydrofurans by isomerizing γ,δ-epoxyalkenes. For example, γ,δ-epoxyalkenes may be isomerized to 2,5-dihydrofurans in the liquid phase using a solution of an organotin (IV) iodide and, optionally, an onium iodide, in an inert solvent and a temperature of 100° to 150° C. 2,5-Dihydrofuran may be hydrogenated as described in U.S. Pat. No. 4,962,210 to tetrahydrofuran, a valuable compound useful as a chemical process solvent and as an intermediate in the preparation of polymers such as poly(tetramethylene ether)glycol.

U.S. Pat. No. 5,315,019 describes a particularly convenient means for the preparation of 2,5-dihydrofurans by the isomerization of γ,δ-epoxyalkenes. The process of U.S. Pat. No. 5,315,019 comprises a liquid phase, continuous process wherein a γ,δ-epoxyalkene initially is fed to a melt of the catalyst system, or a homogeneous mixture of a melt of the catalyst and the 2,5-dihydrofuran product, and thereafter is continuously fed to a solution of the catalyst in a process solvent comprising the 2,5-dihydrofuran product and an oligomer of the γ,δ-epoxyalkene reactant. The 2,5-dihydrofuran product may be recovered from the mixture by conventional distillation procedures. A catalyst system which has been found to be especially effective comprises an onium iodide compound such as an ammonium or phosphonium iodide and an organotin iodide compound such as a trihydrocarbyltin iodide.

U.S. Pat. No. 5,238,889 discloses that α,β-unsaturated carbonyl compounds such as croton-aldehyde (about 0.5–3%) and an oligomer of the γ,δ-epoxyalkene (about 1–6%) are unavoidable side products of the isomerization of γ,δ-epoxyalkenes to 2,5-dihydrofurans. The α,β-unsaturated carbonyl compound by-product is removed from the reaction mixture as a vapor during product recovery. However, the oligomer is non-volatile and accumulates in the catalyst solution, increasing the volume and viscosity of the catalyst solution and decreasing catalyst concentration. Thus, U.S. Pat. No. 5,238,889 provides an efficient process for the separation of expensive catalyst components from the above-described oligomer which permits batch, semi-continuous or continuous operation of the isomerization reaction. The catalyst/oligomer separation is accomplished by a liquid-liquid extraction process in which the catalyst compounds are preferentially extracted from the catalyst/oligomer mixture. The catalyst/extractant phase is separated from the oligomer phase and the solvent removed to give a catalyst mixture which may be reused in the isomerization reaction.

It has now been found that the organotin (IV) iodide isomerization catalyst partially decomposes during the isomerization process through the loss of iodine to an iodine-free organotin (IV) compound which is not catalytically active. Consequently, to maintain the rate of reaction or conversion, it is necessary to add new organotin (IV) iodide to the isomerization reactor(s). It is apparent that the addition of fresh, expensive organotin (IV) iodide can be avoided, or at least minimized, if the iodine-free organotin (IV) compound can be conveniently converted back to the catalytically active organotin (IV) iodide.

It has now been discovered that an iodine-free organotin (IV) compound resulting from the decomposition of an organotin (IV) iodide during the catalytic isomerization of γ,δ-epoxyalkenes to dihydrofurans may be readily converted to the catalytically active organotin (IV) iodide by intimately contacting a catalyst mixture comprising (i) an organotin (IV) iodide, (ii) an iodine-free organotin (IV) compound resulting from the decomposition of the organotin (IV) iodide of component (i), and (iii) a solvent selected from hydrocarbons and chlorocarbons with aqueous hydrogen iodide (HI). During the reactivation process, the iodine-free organotin (IV) compound is restored to its iodide precursor (i) and the organotin (IV) iodide may be reused in the isomerization process as described in U.S. Pat. No. 5,315,019. In a variation of the present process, the described catalyst mixture may be contacted with HI gas to convert the iodine-free organotin (IV) to the corresponding organotin (IV) iodide.

The catalyst regeneration process of the present invention may be carried out at temperatures of about 20° to 150° C., preferably about 50° to 90° C. Normally, the process is operated at approximately ambient pressure although the use of certain combinations of solvents and temperatures may require the use of elevated pressure, e.g., pressures up to about 10 bars absolute.

The HI concentration of the aqueous hydrogen iodide is not critical and may be quite dilute. Indeed, dilute solutions generally are preferred in order to obtain sufficient volume of the aqueous phase for good mixing during, and separation of the phases at the end of, the reaction. Concentrations of hydrogen iodide in water between about 1 and 57 weight percent, preferably between about 2 and 10 weight percent give satisfactory results. The volume ratio of the aqueous hydrogen iodide to the catalyst solution used may be in the range of about 0.1:1 to 10:1, preferably about 0.2:1 to 1:1. The molar ratio of HI present in the aqueous HI used relative to the iodine-free organotin (IV) compound (ii) present in the mixture should be at least 1:1 and preferably is about 1:1 to 6:1.

The time required for full reactivation of the catalyst, i.e., substantially complete conversion of iodine-free organotin (IV) compound to the corresponding organotin (IV) iodide, will vary to some extent, depending upon the solvent used, the reaction temperature, and the efficiency of agitation of the two-phase reaction mixture. In general, however, at a temperature of about 70° C., a contact time of at least 20 minutes between aqueous hydrogen iodide and the catalyst mixture will be required. The contact time between the aqueous hydrogen iodide and the organic catalyst mixture may be in the range of about 10 to 180 minutes. As stated above, the catalyst mixture used in the present invention comprises (i) an organotin (IV) iodide, (ii) an iodine-free organotin (IV) compound resulting from the decomposition of the organotin (IV) iodide of component (i), and (iii) a solvent selected from hydrocarbons and chlorocarbons with aqueous hydrogen iodide. This mixture may be obtained by means of the process described in U.S. Pat. No. 5,238,889. As the examples demonstrate, a variety of solvents for the catalyst system may be used, providing only that they do not react with the catalyst and that they are immiscible with and do not react with aqueous hydrogen iodide. It is generally convenient and most economical to use the same solvent for reactivation as is used for extraction of the catalyst from oligomer. Thus, component (iii) of the catalyst solution may be selected from one or more of the extraction solvents described in U.S. Pat. No. 5,238,889. Examples of such solvents include cyclic and straight- and branched-chain, acyclic alkanes containing from about 5 to 16 carbon atoms. Specific examples of the acyclic alkane solvents include pentane, hexane, heptane, octane, nonane, decane, mixed hexanes, mixed heptanes, mixed octanes, isooctane, Stoddard solvent, and the like. Examples of the cycloalkane solvents include cyclopentane, cyclohexane, cycloheptane, cyclooctane, methylcyclohexane, etc. Alkenes such as hexenes, heptenes, octenes, nonenes and decenes; aromatic hydrocarbons such as benzene, toluene, xylene, mesitylene; and chlorocarbons such as carbon tetrachloride also may be used as solvents. Useful solvents also include various aliphatic petroleum distillate mixtures such as Solvent 140, a mixture consisting of approximately 75–85% $C_{10}$–$C_{11}$ hydrocarbons, 15% $C_8$–$C_9$ hydrocarbons and 5% $C_{12}$–$C_{16}$ hydrocarbons. Other hydrocarbon mixtures which may be used are ligroin and mineral spirits. The preferred solvents are alkanes, preferably straight-chain alkanes, having about 6 to 16 carbon atoms, e.g., hexane, heptane, octane, nonane, and decane, and aliphatic petroleum distillate mixtures. The catalyst mixture used in the invention may comprise either a solution or slurry of components (i) and (ii) described above.

The need for the reactivation process can be determined by analyzing a sample of a mixture of (i) the organotin (IV) iodide and (ii) the iodine-free organotin (IV) compound resulting from the decomposition of the organotin (IV) iodide of component (i). For example, a loss in catalytic activity of a catalyst mixture containing tri-n-octyltin iodide is accompanied by a broadening of the organotin iodide resonances in the $^{13}$C NMR spectrum at approximately 18.5, 26.5, and 33 ppm, and a corresponding loss of iodine content, as indicated by X-ray fluorescence spectroscopy. Typically, the mole percent of organotin (IV) iodide (i) which is decomposed to iodine-free organotin (IV) compound (ii) during the catalytic isomerization of γ,δ-epoxyalkenes to 2,5-dihydrofurans is in the range of about 0.2 to 0.5 per day of operation of the isomerization process. Although the reason for the loss of catalytic activity has not been established, it is probable that iodine is lost gradually from the organotin (IV) iodide by exposure to water in the feed resulting in the formation of volatile hydrogen iodide and an organotin oxide, i.e., an oxide containing the residue

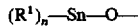

or the analogous hydroxide compound. For example, tri-n-octyltin iodide reacts with water according to the reaction:

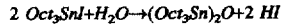

Similarly, di-n-octyltin diiodide reacts with water to produce di-n-octyltin oxide according to the reaction:

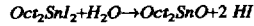

Di-n-octyltin oxide is known to be a polymeric compound having the structure $(Oct_2SnO)_n$. See, for example, A. J. Bloodworth, A. G. Davies, Organotin Compounds, A. K. Sawyer, Ed., Vol. 1, pp 209–211, Marcel Dekker, Inc., N.Y. (1971). Although tin oxides of this kind, i.e., the polymeric organotin oxides, have limited solubility, they still are converted by the process of this invention to the desired tin iodide catalysts.

The organotin (IV) iodide may be selected from hydrocarbyltin triiodides, di(hydrocarbyl)tin diiodides, and tri (hydrocarbyl)tin iodides. Examples of such organotin (IV) iodide compounds have the general formula

wherein each $R^1$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms; and n is 1, 2, or 3.

Specific examples of the organotin compounds include di-n-butyltin diiodide, tri-n-butyltin iodide, tri-n-octyltin iodide, triphenyltin iodide, trimethyltin iodide, n-butyltin triiodide, tricyclohexyltin iodide, tris-(2-methyl-2-phenylpropyl)tin iodide, tribenzyltin iodide, dioctyltin diiodide, dicyclohexyltin diiodide and diphenyltin diiodide. Other organotin halides such as chlorides and bromides may be used in the process wherein they are converted to the iodide compounds. The preferred organotin iodide compounds have the general formula:

wherein each $R^1$ independently is selected from alkyl having about 4 to 10 carbon atoms or phenyl. Tri-n-octyltin iodide and triphenyltin iodide are especially preferred. The iodide compounds of formula (I) generally are soluble in hydrocarbon and chlorocarbon solvents as are the iodide-free compounds resulting from the decomposition of the compounds of formula (II). However, the iodine-free compounds resulting from the decomposition of compounds of formula (I) wherein n is less than 3, particularly when n is 2, typically exhibit limited solubility in hydrocarbon and chlorocarbon solvents. Thus, the catalyst mixture used in the present invention may be either a homogeneous solution or a slurry.

The organotin (IV) iodide may be used in combination with an onium iodide compound to catalyze the isomerization of γ,δ-epoxyalkenes to 2,5-dihydrofurans. When used as a co-catalyst, the onium iodide compound is present in the catalyst solution utilized in the present invention. The onium iodide compound may be selected from a variety of tetra (hydrocarbyl)ammonium iodides and tetra(hydrocarbyl) phosphonium iodides, preferably having a total carbon atom content of about 16 to 72 carbon atoms. Such compounds have the formulas

wherein each $R^2$ substituent independently is selected from alkyl of up to about 20 carbon atoms and each $R^3$ substituent is independently selected from R², benzyl, phenyl or phenyl substituted with up to 3 substituents selected from lower alkyl, e.g., alkyl of up to about 4 carbon atoms, lower alkoxy or halogen; or two R² substituents collectively may represent alkylene of 4 to 6 carbon atoms including alkylene of 4 to 6 carbon atoms substituted with lower alkyl; provided, as specified above, that the quaternary iodide compounds contain about 16 to 72 carbon atoms. Specific examples of the onium iodide catalyst component include tetra-n-octylphosphonium iodide, tri-n-octyl(n-dodecyl)-phosphonium iodide, tri-n-octyl(n-hexadecyl)phosphonium iodide, tri-n-octyl(n-octadecyl)phosphonium iodide, tetra-n-dodecylphosphonium iodide, tetra-n-hexadecylphosphonium iodide, tetra-n-octadecylphosphonium iodide, tetra-n-dodecylammonium iodide, tetra-n-hexadecylammonium iodide, and tetra-n-octadecylammonium iodide. The preferred onium iodides are tetra-n-alkylphosphonium iodides containing about 32 to 72 carbon atoms, especially compounds of formula (IV) above wherein each R³ is straight-chain alkyl of about 4 to 18 carbon atoms. Tetra-n-dodecylphosphonium iodide, tetra-n-hexadecylphosphonium iodide, and tri-n-octyl(n-octadecyl) phosphonium iodide are especially preferred.

The ratio of the onium iodide and organotin (IV) iodide can vary substantially depending, for example, upon the particular compounds used. Generally, the quaternary onium iodide:organotin (IV) iodide mole ratio is within the range of about 20:1 to 0.05:1. For the preferred catalyst system comprising a phosphonium iodide and an organotin iodide, a phosphonium iodide:organotin iodide mole ratio of about 5:1 to 0.2:1 is especially preferred.

The catalyst reactivation process of the present invention may be operated in conjunction with the oligomer separation process disclosed in U.S. Pat. No. 5,238,889. Accordingly, a second embodiment of the present invention involves the separation and reactivation of a catalyst mixture comprising (i) an organotin (IV) iodide compound, (ii) an iodine-free organotin (IV) compound resulting from the decomposition of the organotin (IV) iodide of component (i) and, optionally, (iii) an onium iodide compound, from a mixture of the catalyst system and an oligomer of a γ,δ-epoxyalkene by the steps comprising:

(1) intimately contacting the mixture of the catalyst system and an oligomer of a γ,δ-epoxyalkene with an extraction solvent selected from hydrocarbons and chlorocarbons;
(2) allowing the mixture of step (1) to phase separate;
(3) recovering the extraction solvent phase containing compounds (i), (ii) and, optionally, (iii); and
(4) intimately contacting the extraction solvent phase of step (3) with aqueous hydrogen iodide, whereby iodine-free organotin (IV) compound (ii) is converted to organotin (IV) iodide compound (i).

The extraction solvent phase recovered in step (3) contains substantially less oligomer than is contained in the mixture specified in step (1). For example, less than 70 weight percent, typically about 25 to 60 weight percent, of the oligomer present in the starting mixture of step (1) is present in the extraction solvent phase of step (3). The 4-step separation/reactivation process of this invention may give enhanced or increased oligomer removal when, at the conclusion of step (4), additional dissolved oligomer separates from the extraction solvent.

As described in U.S. Pat. No. 5,238,889, the oligomer referred to in the above process description is formed as a non-volatile, by-product of an isomerization process wherein the γ,δ-epoxyalkene is isomerized to the corresponding 2,5-dihydrofuran. The isomerization process typically is carried out by heating, e.g., at temperatures in the range of about 65° to 160° C., the γ,δ-epoxyalkene in the liquid phase in the presence of a catalyst system comprising an organotin (IV) iodide compound (i) and, optionally, an onium iodide compound (iii). The oligomer is a low molecular weight polyether formed as the result of ring-opening polymerization of the γ,δ-epoxyalkene reactant in a manner analogous to the formation of polyether oligomers and polymers from ethylene oxide and propylene oxide.

The extraction solvent (extractant) employed may be selected from the hydrocarbons and chlorocarbons described hereinabove as solvents for the reactivation process. Generally, the extractant should satisfy four requirements: (1) it should form a separate liquid phase at equilibrium when contacted with a mixture of the catalyst components and the oligomer, (2) it should have a higher selectivity for dissolving the catalyst component(s) than the oligomer, (3) it should have characteristics that enable it to be separated from the catalyst components by evaporation, distillation, crystallization, or some other separation operation, and (4) it should be inert to the catalyst components, starting material and products. It is possible that an extraction solvent may function both as the solvent for the isomerization reaction and the oligomer removal process if the 2,5-dihydrofuran product is removed prior to phase separation. In general, the extraction solvent should be non-polar to avoid dissolving the oligomer. The extraction solvent may comprise a mixture of two or more solvents. The preferred extraction solvents are alkanes having about 6 to 16 carbon atoms, e.g., hexane, heptane, octane, nonane, and decane, and aliphatic petroleum distillate mixtures.

The concentration of the organotin iodide compound and, optionally, onium iodide compound in the oligomer material which is extracted in accordance with our invention typically is in the range of about 20 to 90 weight percent based on the total weight of the catalyst/oligomer mixture. The amount of extraction solvent employed can vary substantially depending, for example, on the particular onium iodide and organotin iodide compounds present in the oligomer material, the extraction solvent being used, and the manner in which the extraction process is operated. However, the weight ratio of the extraction solvent to the catalyst/oligomer mixture to be extracted normally is in the range of about 10:1 to 0.1:1.

The oligomer material involved in the second embodiment of the invention is an unavoidable side product of the isomerization of γ,δ-epoxyalkenes to 2,5-dihydrofurans utilizing the above-described organotin (IV) iodide compounds and, optionally, onium compounds as catalysts. The γ,δ-epoxyalkene reactants may contain from 4 to about 8 carbon atoms. Examples of the epoxyalkene and epoxycycloalkene reactants include compounds having the structural formula:

wherein each R⁴ is independently selected from hydrogen and methyl or 2 R⁴ substituents collectively may represent an alkylene radical which forms a ring having about 5 to 8 carbon atoms. The preferred epoxyalkene reactants comprise compounds of formula (V) wherein a maximum of four of the R⁴ substituents individually may represent methyl. Exemplary compounds contemplated for use in the practice of the present invention include 3,4-epoxy-3-methyl-1-butene, 3,4-epoxy-2-methyl-1-butene, 2,3-dimethyl-3,4- epoxy-1-butene, 3,4-epoxy-1-butene, 2,5-dimethyl-2,4-hexadiene monoepoxide, 3,4-epoxycyclooctene and the like. The epoxyalkene reactant of primary interest is 3,4-epoxy-1-butene.

The 2,5-dihydrofuran compounds obtained have the structural formula:

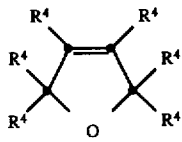

(VI)

wherein the $R^4$ substituents are defined above. The most important compound is 2,5-dihydrofuran.

The process of the present invention is further illustrated by the following examples.

EXAMPLE 1

The catalyst-containing material used in this experiment was isomerization reaction mixture comprising tri-n-octyltin iodide, an iodide-free tri-n-octyltin compound resulting from the decomposition of the tri-n-octyltin iodide and tri-n-octyl(octadecyl)phosphonium iodide. The material was recovered from a process in which 3,4-epoxy-1-butene was isomerized to 2,5-dihydrofuran according to the procedure of U.S. Pat. No. 5,315,019 and had been subjected to the oligomer separation process described in U.S. Pat. No. 5,238,889. The catalyst-containing material (25 g) was stirred in 50 mL of heptane and heated to 70° C. A small lower layer (0.9 g) of oily, insoluble oligomer was removed. The heptane solution then was stirred and heated at 70° C. with an approximately 2.5 weight percent aqueous solution of hydrogen iodide (7.0 g of 10 weight percent aqueous hydrogen iodide in 20 mL of water) for 30 minutes. Stirring was stopped and the mixture was allowed to phase separate. The water layer was removed, as well as an additional 8.8 g of oligomer which separated from the heptane solution. The heptane solution was washed with three 50-mL portions of distilled water; the pH of the final wash was 4. Heptane was stripped from the reactivated catalyst on a rotary vacuum evaporator at 85°–95° C., first under water aspirator vacuum, then with a mechanical vacuum pump. The residual reactivated catalyst, which weighed 15.3 g, was analyzed by $^{13}C$ nuclear magnetic resonance spectroscopy (CDCl$_3$ solvent) and X-ray fluorescence (XRF) spectroscopy. Comparison of the organotin iodide resonances in the $^{13}C$ NMR spectra of the starting, partially-deactivated catalyst and reactivated catalysts with those of fresh, fully-active catalyst showed that the reactivated catalyst had been restored to its original condition. XRF analysis and calculation of the atomic ratio of iodine to (tin+phosphorus) showed restoration of the atomic ratio to 0.98. Fully-active catalyst has a theoretical atomic ratio of iodine to (tin+phosphorus) equal to one. The results of analyses of deactivated and reactivated catalyst are shown in Table I. The reactivated catalyst was used for the isomerization in a small continuous reactor and found to have regained its original activity.

EXAMPLE 2

This example illustrates the reactivation of the catalyst using Solvent 140, an aliphatic petroleum distillate mixture (defined above) sold by Ashland Chemical Company. The procedure of Example 1 was repeated using a 25 g sample of the same catalyst-containing material, 50 mL of Solvent 140, 8.5 mL of 10 weight percent hydrogen iodide, and 20 mL of water. Approximately 1 g of sodium iodide was added at the end of the reaction to assist in breaking the emulsion which formed between the water and oligomer layers. The water layer was removed and the hydrocarbon solution was washed at 70° C. with three 50-mL portions of water, and the solvent was evaporated as before. Analysis by XRF and $^{13}C$ NMR indicated full reactivation of the catalyst. The analytical results are shown in Table I.

EXAMPLE 3

This example illustrates how the atomic ratio of iodine to (tin+phosphorus) in the catalyst increases with time during treatment with aqueous hydrogen iodide. The catalyst-containing material used in this experiment was isomerization reaction mixture, similar to that used in Examples 1 and 2, comprising tri-n-octyltin iodide, an iodide-free tri-n-octyltin compound resulting from the decomposition of the tri-n-octyltin iodide and tri-n-octyl (octadecyl)phosphonium iodide. The material was recovered from a process in which 3,4-epoxy-1-butene was isomerized to 2,5-dihydrofuran according to the procedure of U.S. Pat. No. 5,315,019 and had been subjected to the oligomer separation process described in U.S. Pat. No. 5,238,889. A solution of 25 g of the catalyst-containing material in 50 mL of octane was warmed, with stirring, to 70° C.; then 54.6 g of 10 weight percent aqueous hydrogen iodide was added. At 10 minute intervals, stirring was stopped, the mixture was allowed to settle, and a sample of the organic layer taken for X-ray fluorescence analysis. The results are summarized in Table II wherein "Reaction Time" is the total contact time between the partially-deactivated catalyst and the aqueous hydrogen iodide solution. The "Final" sample analyzed was taken after 30 minutes of reaction time, a water wash and evaporation as described in Example 1.

TABLE I

|  | XRF | | | Atomic % | | | Atomic Ratio |
|---|---|---|---|---|---|---|---|
|  | % I | % Sn | % P | % I/ 126.9 | % Sn/ 118.7 | % P/ 31.0 | I/(Sn + P) |
| EXAMPLE 1 | | | | | | | |
| Deactivated cat. | 5.8 | 3.8 | 0.87 | 0.046 | 0.032 | 0.028 | 0.77 |
| Reactivated cat. | 11.39 | 5.85 | 1.33 | 0.090 | 0.049 | 0.043 | 0.98 |
| EXAMPLE 2 | | | | | | | |
| Deactivated cat. | 5.8 | 3.8 | 0.87 | 0.046 | 0.032 | 0.028 | 0.77 |
| Reactivated cat. | 12.97 | 6.48 | 1.49 | 0.102 | 0.055 | 0.048 | 0.99 |

TABLE II

| Reaction Time | XRF | | | Atomic % | | | Atomic Ratio |
|---|---|---|---|---|---|---|---|
|  | % I | % Sn | % P | % I/ 126.9 | % Sn/ 118.7 | % P/ 31.0 | I/(Sn + P) |
| Start | 5.17 | 2.77 | 0.66 | 0.041 | 0.023 | 0.021 | 0.93 |
| 10 | 6.12 | 2.78 | 0.65 | 0.048 | 0.023 | 0.021 | 1.09 |
| 20 | 6.47 | 2.81 | 0.68 | 0.051 | 0.024 | 0.022 | 1.11 |
| 30 | 6.53 | 2.81 | 0.66 | 0.051 | 0.024 | 0.021 | 1.13 |
| Final | 15.11 | 6.54 | 1.57 | 0.12 | 0.055 | 0.051 | 1.13 |

EXAMPLE 4

This example illustrates reactivation of catalyst after use in a continuous reactor, in which the conversion of 3,4- epoxy-1-butene had fallen from about 90% to 76–78%. As used herein, conversion means mole percent conversion of 3,4-epoxy-1-butene defined as:

$$\frac{\text{Moles 3,4-epoxy-1-butene converted to products}}{\text{Moles 3,4-epoxy-1-butene fed}} \times 100$$

The catalyst containing material was the same as that used in Example 3. Catalyst-containing material (800 g) and 1600 mL of n-octane were placed into a 5000-mL, three-neck, round-bottom flask fitted with a stirrer, thermometer, condenser, and bottom stopcock, and maintained under a nitrogen atmosphere. The mixture was heated to 70° C. and maintained at 70° C. with stirring for one hour. Stirring was stopped, the mixture was allowed to settle, and 32 g of the bottom layer (oligomer) was removed.

A solution of 320 mL of 10% aqueous hydrogen iodide and 640 mL of water was added; the pH of this solution was 1.0. The mixture was heated at 70° C. with stirring for 45 minutes, then stirring was stopped and the bottom layer (pH about 3) was removed and discarded. The octane solution was stirred with 1500 mL of water at 70° C. for 15 minutes then allowed to settle and the bottom layer removed along with approximately 80 g of an interfacial emulsion. The octane solution was washed twice with 1500-mL portions of water at 70° C. for 15 minutes. The pH of the final wash water was about 5. The octane was removed on a rotary vacuum evaporator. The final weight of the recovered, reactivated catalyst was 575.2 g.

The reactivated catalyst was placed back into the continuous reactor (1000-mL, jacketed reactor which was heated by hot ethylene glycol, and fitted for removal of volatile material overhead through a 12-plate Oldershaw distillation column). 3,4-Epoxy-1-butene was fed continuously to the reactor through a drying bed of 3A molecular sieves, while product 2,5-dihydrofuran was removed through the distillation column, which was operated at a 2:1 reflux ratio. Conversion of 3,4-epoxy-1-butene to 2,5-dihydrofuran during the first 50 hours of continuous operation was approximately 88–89%, as compared with 76–78% conversion prior to reactivation in the same reactor under the same conditions.

EXAMPLE 5

This example simulates the regeneration of tri-n-butyltin iodide catalyst from the corresponding iodine-free bis(tri-n-butyltin)oxide. A solution of 11.93 g of bis(tri-n-butyltin) oxide in 200 mL of toluene was stirred and heated to 70° C. A 9% aqueous hydrogen iodide solution (87 g) was added to the solution and the mixture stirred at 70° C. for three hours. Stirring was stopped and the mixture was allowed to phase separate. The aqueous layer was discarded. The toluene solution was washed once with 100 mL of 1% aqueous hydrogen iodide. GC analysis of the resulting toluene solution showed the presence of tri-n-butyltin iodide. The solvent was stripped from the catalyst on a rotary vacuum evaporator at about 45° C. under water aspirator vacuum. The resulting reactivated catalyst weighed 16.5 g (theory 16.7 g).

EXAMPLE 6

This example simulates the regeneration of tricyclohexyltin iodide catalyst from the corresponding iodine-free compound. A slurry of 7.78 g of tricyclohexyltin hydroxide and 100 mL of octane was stirred and heated to 70° C. A 4.5% aqueous hydrogen iodide solution (82.9 g) was added to the slurry and the mixture stirred at 70° C. for 105 minutes. Stirring was stopped and the mixture was allowed to phase separate. The water layer was discarded. The octane solution was washed three times with 100 mL of distilled water (discarding interfacial emulsion). GC analysis of the resulting octane solution showed the presence of tricyclohexyltin iodide. The solvent was stripped from the catalyst on a rotary vacuum evaporator at about 55° C. under water aspirator vacuum. The resulting reactivated catalyst solidified upon cooling and had a weight of 9.41 g (theory 10.0 g). The melting point of the solid was 64°–65° C. (literature melting point for tricyclohexyltin iodide is 65° C. (E. Krause and R. Pohland, Chem. Ber., 57, 522 (1924)).

EXAMPLE 7

This example simulates the regeneration of di-n-octyltin diiodide catalyst from the corresponding iodine-free compound. A slurry of 7.22 g of di-n-octyltin oxide and 100 mL of toluene was stirred and heated to 70° C. A 9% aqueous hydrogen iodide solution (87 g) was added to the slurry and the mixture stirred at 70° C. for one hour. Stirring was stopped, another 100 mL of toluene was added; then the mixture was allowed to phase separate. The water layer and interfacial emulsion were discarded. The toluene solution was washed once with 100 mL of distilled water. GC analysis of the resulting toluene solution showed the presence of di-n-octyltin diiodide catalyst. The solvent was stripped from the catalyst on a rotary vacuum evaporator at about 55° C. under water aspirator vacuum. The resulting reactivated catalyst weighed 8.63 g (theory 11.98 g).

The invention has been described in detail with particular reference to preferred embodiments thereof, but it will be understood that variations and modifications can be effected within the spirit and scope of the invention.

We claim:

1. Process for converting an iodine-free organotin (IV) compound resulting from the decomposition of an organotin (IV) iodide during the catalytic isomerization of γ,δ-epoxyalkenes to 2,5-dihydrofurans to the corresponding, catalytically active organotin (IV) iodide which comprises intimately contacting a catalyst mixture comprising (i) an organotin (IV) iodide, (ii) an iodine-free organotin (IV) compound resulting from the decomposition of the organotin (IV) iodide of component (i), and (iii) a solvent selected from hydrocarbons and chlorocarbons with aqueous hydrogen iodide.

2. Process according to claim 1 wherein the process is carried out at a temperature of about 20° to 150° C. using aqueous hydrogen iodide wherein the hydrogen iodide concentration is about 1 to 57 weight percent.

3. Process according to claim 1 wherein the process is carried out at a temperature of about 50° to 90° C. using aqueous hydrogen iodide wherein the hydrogen iodide concentration is about 2 to 10 weight percent and the volume ratio of the aqueous hydrogen iodide to the catalyst solution is about 0.1:1 to 10:1 and the molar ratio of hydrogen iodide present in the aqueous hydrogen iodide used relative to the iodine-free organotin (IV) compound (ii) present in the solvent is about 1:1 to 6:1.

4. Process according to claim 1 wherein organotin (IV) iodide (i) has the formula

wherein each $R^1$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms;

n is 1, 2, or 3; and wherein iodine-free organotin (IV) compound (ii) is an organotin (IV) oxide containing the residue

$(R^1)_n$—Sn—O—.

5. Process for converting an iodine-free organotin (IV) compound resulting from the decomposition of an organotin (IV) iodide during the catalytic isomerization of γ,δ-epoxyalkenes to 2,5-dihydrofurans to the corresponding, catalytically active organotin (IV) iodide which comprises intimately contacting a catalyst solution comprising:

(i) an organotin (IV) iodide having the formula

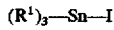

$(R^1)_3$—Sn—I    (I)

wherein $R^1$ is selected from alkyl having about 4 to 10 carbon atoms or phenyl;

(ii) an iodine-free organotin (IV) compound resulting from the decomposition of the organotin (IV) iodide of component (i) which is an organotin (IV) oxide containing the residue

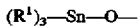

$(R^1)_3$—Sn—O— and (iii) a solvent selected from hydrocarbons and chlorocarbons;

with aqueous hydrogen iodide.

6. Process according to claim 5 wherein the process is carried out at a temperature of about 50° to 90° C. using aqueous hydrogen iodide wherein the hydrogen iodide concentration is about 2 to 10 weight percent; the volume ratio of the aqueous hydrogen iodide to the catalyst solution is about 0.1 to 10:1; the molar ratio of hydrogen iodide present in the aqueous hydrogen iodide used relative to the iodine-free organotin (IV) compound (ii) present in the solvent is about 1:1 to 6:1; and the solvent is an alkane having about 6 to 16 carbon atoms or an aliphatic petroleum distillate mixture.

7. Process according to claim 6 wherein the catalyst solution includes a tetra(hydrocarbyl)ammonium iodide or a tetra(hydrocarbyl)phosphonium iodide.

8. Process for the separation and reactivation of a catalyst mixture comprising (i) an organotin (IV) iodide compound, (ii) an iodine-free organotin (IV) compound resulting from the decomposition of the organotin (IV) iodide of component (i) from a mixture of the catalyst system and an oligomer of a γ,δ-epoxyalkene by the steps comprising:

(1) intimately contacting the mixture of the catalyst system and an oligomer of a γ,δ-epoxyalkene with an extraction solvent selected from hydrocarbons and chlorocarbons;

(2) allowing the mixture of step (1) to phase separate;

(3) recovering the extraction solvent phase containing compounds (i) and (ii); and (4) intimately contacting the extraction solvent phase of step (3) with aqueous hydrogen iodide, whereby iodine-free organotin (IV) compound (ii) is converted to organotin (IV) iodide compound (i).

9. Process according to claim 8 wherein step (4) is carried out at a temperature of about 50° to 90° C. using aqueous hydrogen iodide wherein the hydrogen iodide concentration is about 2 to 10 weight percent; the volume ratio of the aqueous hydrogen iodide to the catalyst solution is about 0.1 to 10:1; the molar ratio of hydrogen iodide present in the aqueous hydrogen iodide used relative to the iodine-free organotin (IV) compound (ii) present in the solvent is about 1:1 to 6:1; and the solvent is an alkane having about 6 to 16 carbon atoms or an aliphatic petroleum distillate mixture.

10. Process according to claim 9 wherein the organotin (IV) iodide has the formula

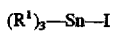

$(R^1)_3$—Sn—I    (I)

wherein $R^1$ is selected from alkyl having about 4 to 10 carbon atoms or phenyl; and the iodine-free organotin (IV) compound is an organotin (IV) oxide containing the residue

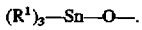

$(R^1)_3$—Sn—O—.

* * * * *